United States Patent [19]

Kadlecik et al.

[11] 4,044,226
[45] Aug. 23, 1977

[54] APPARATUS FOR DISINFECTION OF HYDROPHILIC CONTACT LENSES

[75] Inventors: John Kadlecik, Macedon; Wayne R. Manning, Victor, both of N.Y.

[73] Assignee: Bausch & Lomb Incorporated, Rochester, N.Y.

[21] Appl. No.: 718,729

[22] Filed: Aug. 30, 1976

Related U.S. Application Data

[63] Continuation-in-part of Ser. No. 597,125, July 18, 1975, abandoned.

[51] Int. Cl.² .......................... A61L 3/00; F24C 1/16
[52] U.S. Cl. .......................... 219/521; 21/2; 21/85; 21/86; 21/93; 126/275 E; 219/451
[58] Field of Search ........... 21/2, 85, 86, 87, 93; 219/201, 200, 385–387, 412, 413, 430, 435–442, 489, 490, 494, 508, 510, 520, 522; 99/325, 331, 333, 426, 440, 441; 126/211, 217, 220, 273 R, 275 E

[56] References Cited

U.S. PATENT DOCUMENTS

| 2,806,123 | 9/1957 | Steinbock | 126/275 E X |
|---|---|---|---|
| 2,817,744 | 12/1957 | Free | 219/439 X |
| 2,924,167 | 2/1960 | Rhodes | 219/295 X |
| 3,278,256 | 10/1966 | Skaller | 21/85 X |
| 3,280,304 | 10/1966 | Shinohara et al. | 219/437 X |
| 3,413,440 | 11/1968 | Drugmand | 219/437 X |
| 3,801,278 | 4/1974 | Wagner et al. | 21/86 |
| 3,814,900 | 6/1974 | Frey et al. | 219/385 |
| 3,983,362 | 9/1976 | Hoogesteger et al. | 21/85 X |

*Primary Examiner*—Barry S. Richman
*Attorney, Agent, or Firm*—Frank C. Parker; Myron B. Kurtzman

[57] ABSTRACT

Process and apparatus for disinfection of hydrophilic contact lenses by controlled exposure of the lenses to heat. In the apparatus is a compartment formed by a heat storage-transfer combination. The compartment forming combination is heated by means of a heating element. The heat is transferred to a contact lens carrying case received in the compartment. The heat is maintained at temperatures and for a period of time sufficient to disinfect hydrophilic contact lenses contained in the carrying case.

14 Claims, 5 Drawing Figures

APPARATUS FOR DISINFECTION OF HYDROPHILIC CONTACT LENSES

CROSS REFERENCES TO RELATED APPLICATIONS

This application is a continuation-in-part of U.S. application Ser. No. 597,125, filed July 18, 1975 and now abandoned.

Application Ser. No. 597,124 entitled Contact Lens Asepticizing Circuit of Kurt H. Kreckel filed July 18, 1975.

Application Ser. No. 490,535, filed July 22, 1974, of John Kadlecik and John R. Williams, III entitled Contact Lens Carrying Case and now abandoned.

Design application Ser. No. 490,536, filed July 22, 1974, of Paul A. Hoogesteger and John Kadlecik entitled Design for a Contact Lens Storage Chamber now Design Pat. No. D237416, issued Oct. 20, 1975.

Design application Ser. No. 490,537, filed July 22, 1974, of Paul A. Hoogesteger entitled Design for a Contact Lens Carrying Case now Design Pat. No. D239413, issued Mar. 30, 1976.

Design application Ser. No. 597,126, filed July 18, 1975 of Paul A. Hoogesteger entitled Design for Contact Lens Disinfection Apparatus now Design Pat. No. D243287, issued Feb. 1, 1977.

BACKGROUND OF THE INVENTION

1. Field of the Invention

This invention relates to apparatus for and a process of disinfecting hydrophilic contact lenses. More particularly, this invention relates to a portable apparatus for disinfecting hydrophilic contact lenses.

2. Description of the Prior Art

Hydrophilic contact lenses, being water absorbant, require daily care by the patient in order to destroy pathogenic microorganisms which accumulate on and can contaminate the lenses. Daily care, i.e. disinfection, is necessary, for the microorganisms are a potential source of eye infection if they are not destroyed.

A number of methods have been suggested for disinfecting hydrophilic lenses such as, for example, boiling the lenses immersed in a saline solution for at least 10 minutes at +100° C, or chemically treating the lenses. Boiling, which requires the attention of the patient is a time consuming process and the high temperature treatment can, with the passage of time, have adverse affects upon the lens. Chemical treatment requires the utmost care since after treatment the chemicals must be properly and thoroughly flushed from the lens.

In order to destroy the pathogenic microorganisms, it is sufficient to disinfect the lens.

Disinfection requires that the object to be disinfected be heated at a sufficient temperature and for a sufficient time so as to cause the destruction of pathogenic microorganisms on the lenses.

In U.S. Pat. No. 3,801,278 of Wagner et al., issued Apr. 2, 1974 an apparatus is disclosed for mass sterilization of hydrophilic lenses. The apparatus is particularly designed for the ophthalmologists and optometrists. The patent discloses and teaches that the lenses are to be sterilized. The device is not suitable for home use since it is bulky and designed around the needs of the professional who has to treat lenses in bulk. Because the lenses are sterilized the apparatus is not particularly desirable for constant use by a patient who is involved with treating only a pair of lenses. The device furthermore employs a mechanical timer for controlling its operation.

U.S. Pat. No. 3,720,402 of Cummins et al., issued May 13, 1973 describes a cleaning device for contact lenses. The device, as described, cannot effectively be employed for disinfecting since the temperature requirement for disinfection is not obtained. The device additionally depends on a mechanical timing mechanism for its operation which, if it should not properly function, could result in the evaporation of the cleaning fluid and the concomitant adverse environment for the treated lenses.

U.S. Pat. No. 3,585,362 issued June 15, 1971 describes an apparatus which depends on the rapid conversion of a quantity of water to steam for sterilizing contact lenses. This device and others which similarly depend on the conversion of water to steam for the treatment of hydrophilic contact lenses must be carefully cared for by the patient in order to avoid the corrosion of metal parts as a result of deposits such as iron, calcium, chloride ions and the like if the device is not properly cleaned after each use.

U.S. Pat. No. 3,852,032 of Urbach, issued Dec. 7, 1974, describes a method of sterilization of hydrophilic contact lenses by means of U.V. radiation. In order to avoid embrittlement and disintegration of the polymeric material constituting the contact lens, the lens material must contain ultraviolet stabilizers. The method and apparatus described is not universally applicable for hydrophilic contact lenses since few, if any lenses comprise U.V. stabilizers.

It is therefore desirable to provide a device and method for disinfecting hydrophilic contact lenses which would be applicable for all types of hydrophilic lenses. It is further desirable to provide a device and method which does not depend on the production of steam for the transfer of heat from the apparatus to the lens carrying case and to provide a device which can be carried about in a woman's purse or in a man's shirt pocket said device being free of mechanical timing mechanisms.

SUMMARY OF THE PRESENT INVENTION

In accordance with the present invention, there is provided a disinfecting apparatus for destroying pathogenic microorganisms that may be on and about a contact lens. Disinfection is accomplished by surrounding a contact lens carrying case containing contact lenses, typically hydrophilic contact lenses, with dry, hot air at temperatures and for at least a period of time necessary to destroy pathogenic microorganisms. The apparatus comprises means defining a housing having a cover and a base. The cover and base are movable relative to each other. A well member which is a heat storage-transfer means and adapted to receive a contact lens carrying case is received within the housing and cooperates with the cover to define an insulated compartment for the contact lens carrying case. Heating means such as a heating element enclosed in the housing heats the heat storage-transfer means to a predetermined temperature. The heat absorbed by the heat member is transferred to the carrying case within the compartment at a rate so as to obtain a complete disinfecting cycle of the contact lenses within the carrying case.

The rate of heat transfer from the heat storage-transfer member to the contact lens carrying case containing a contact lens therein is determined by the material employed in the member. For disinfecting contact lenses within a reasonable time it is required that the heat storage-transfer member be constructed from a high density material which is easily cast, coated and has a high heat capacity. The material which can be usefully employed will have a specific heat of about 0.09 to about 0.11 BTU/lb$_m$F° and a density of from about 445 to about 560 b$_m$/ft$^3$. The thermal mass of the member will be about 4 ounces to about 16 ounces. Illustrative of metals that can be usefully employed in accordance with this invention are zinc, brass, steel, copper, grey iron and the like.

Upon obtaining the desired predetermined temperature, the selected metal will continuously release its accumulated heat at a rate and at temperatures so as to cause the interior of a contact lens carrying case to be maintained preferably within a temperature range of from +80° C to about +100° C for at least 10 minutes. Therefore, in accordance with the invention the disinfecting cycle is controlled through the selection of materials of which the heat member is constructed, the weight of the member and the predetermined temperature to which the member is heated.

The use of the dense metal having the proper weight will result in the metal inherently acting as the timing mechanism as well as transferring the heat from the heater to the case. If the material and its weight be such that the absorbed heat is rapidly given up, the interior of the carrying case will not be maintained at the disinfecting cycle. For example, the specific heat of aluminum falls within the range described above, however, its density is lower therefore, for a system which is useful for the patient, aluminum is avoided because it would release the absorbed heat before disinfection can be accomplished. Furthermore, in order to construct the heat storage-transfer means of aluminum and yet provide a device that is of a reasonable size, a low watt rated heater must be employed. This combination of aluminum and low watt heater can at times be ineffective as a disinfecting system since it is greatly affected by surrounding temperature variation and wind drafts.

On the other hand, an exceedingly dense metal would maintain the disinfecting temperature for an unnecessarily long period of time.

Upon the heat member obtaining the predetermined temperature, the heating element is deactivated by means of thermostatically deactivating means. Disinfection will continue since the heat member will continuously release its absorbed heat into the chamber. It is clear that the device does not require a timing mechanism since the interior temperature of the carrying case and the length of time the temperature is maintained is controlled primarily by proper selection of the heat member material and the predetermined temperature.

The predetermined temperature is a function of the material of which the heat member is constructed and its size. The temperature should be selected so as to achieve the release of absorbed heat to the carrying case at a rate which will cause the disinfecting cycle to take place from about 10 to about 25 minutes and preferably from about 15 to about 20 minutes.

The weight of the heat member, in the case of it being constructed of zinc, is in the range of about 23 grams to about 248 grams. A smaller heat member will be more sensitive to ambient conditions, whereas a heavier heat member, as indicated above will maintain the disinfecting temperatures for an unnecessarily long period of time.

The predetermined temperature for a heat member constructed of zinc is about +122° C. For heat members constructed of other metals, the predetermined temperature will be adjusted accordingly in order to obtain the objectives of the invention.

It is a further objective of this invention to provide a process for disinfecting contact lenses contained in a contact lens carrying case by heating the contact lens carrying case by means of dry, hot air to a temperature and for a period of time such that the contact lens contained interior the carrying case is maintained at a disinfecting temperature range for a period of time to disinfect the lens.

By employing the device in accordance with this invention, the use of steam of heat transfer is eliminated, one need not employ chemicals for disinfection, a simple portable device is provided and timing means is provided without employment of mechanical timers.

DESCRIPTION OF THE PREFERRED EMBODIMENTS

Figure 1:
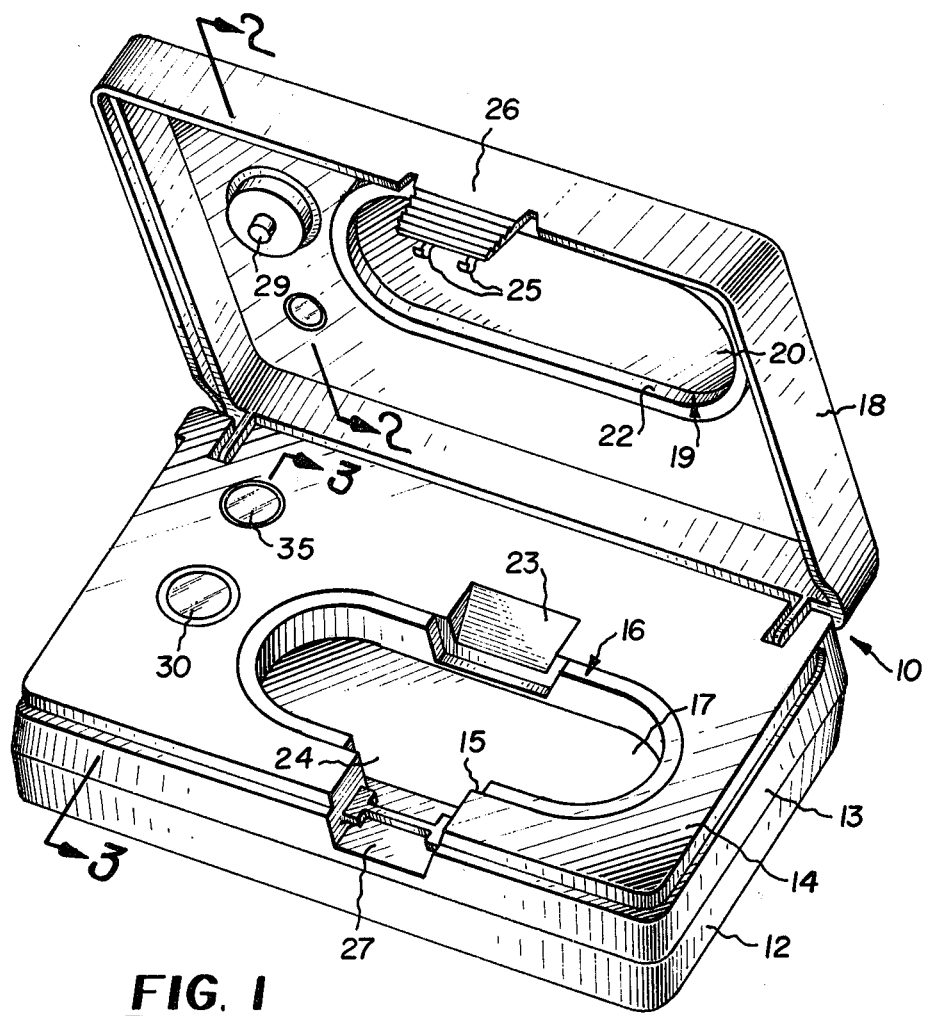
FIG. 1 is a perspective view of the preferred embodiment of the invention.
Figure 2:
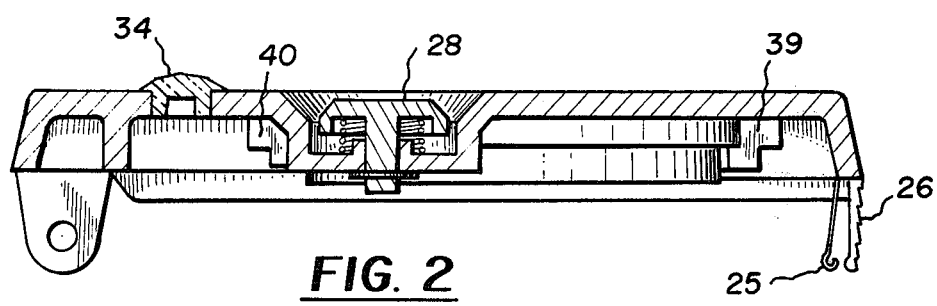
FIG. 2 is a section view along 2—2 of FIG. 1.
Figure 3:
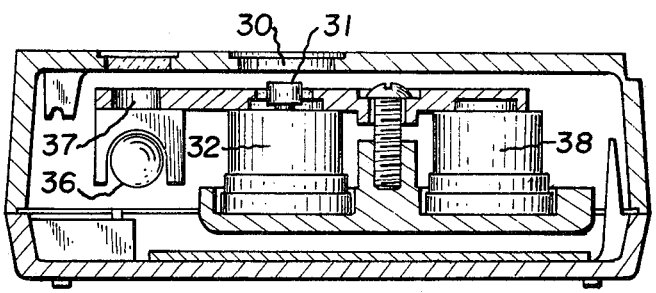
FIG. 3 is a section view along 3—3 of FIG. 1.
Figure 4:
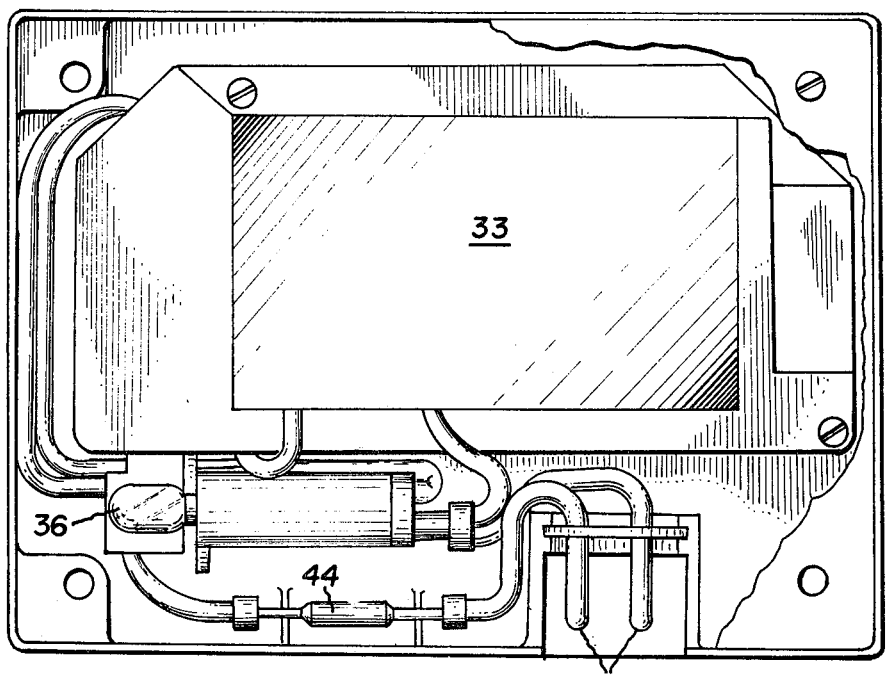
FIG. 4 is a cutaway bottom view of the apparatus of this invention.

Referring to the drawings, FIG. 1, shows the apparatus generally indicated at 10. The apparatus includes a base 12, housing 13 having an upper surface 14 into which an opening 15 is formed. The opening is shaped to receive a bottom portion heat member 16 having a recess or well 17. The heat member 16 and recess 17 are preferably shaped in accordance with the shape of the contact lens carrying case to be received therein. As illustrated in FIG. 1, the recess is shallow and shaped to receive a carrying case wherein two lenses will lie substantially horizontal with respect to each other. Typically the recess will be shaped so as to receive a contact lens carrying case such as that disclosed in U.S. application Ser. No. 490,535, filed July 22, 1974. Should the carrying case be designed so that the lenses lie substantially vertical with respect to each other, the heat member 16 and recess 17 would be shaped so as to form a well. The housing is provided with a suitable closure such as a hinged cover 18. However, the cover can be slidably closed or closable by other methods and means.

In the preferred embodiment of this invention, the cover 18 has molded on its underside and projecting downwardly therefrom rim 22. Rim 22 can be made from any insulating material such as glass filled polyesters, glass filled polycarbonate, nylon and the like. Bottom heat member rim 21 and rim 22 when the cover is in a closed configuration form a compartment shaped to receive a contact lens carrying case.

As another alternative, heat member 16 can be constructed so as to have a flat upper surface and the undersurface of the cover can be recessed so as to surround the top and side portions of the carrying case.

As an alternative the cover 18 has mounted by any suitable means, such as retaining elements 39 and 40, a top portion member 19 having recess 20. The top member can be constructed of any suitable metal.

The rim 21 is cut away at 23 and 24 in order to facilitate the placement in and removal of the carrying case with respect to the recess. A latch 25, latch cover 26 and catch 27 for the latch is provided so as to keep the cover or lid 18 in a secured closed position during the operation of the apparatus. Any other suitable means may be employed in order to secure the cover in a closed position during the operation of the apparatus.

Heat member 16 forming the bottom portion of the disinfecting compartment is heated by means of electrical heating element 33 which is preferably disposed on the underside of said heat member. In the preferred embodiment of the invention heating element 33 is a 25 watt heater. However, higher or lower watt sources can be employed.

By means of starter button 28 disposed in the cover 18 a manual reset thermostat 32 actuates heating element 33. The manual reset thermostat is a manually operable control means for actuating the heating element cooperating with means for thermostatically deactivating the heating element. In order to insure that heating element 33 cannot be actuated while cover or lid 18 is in an open mode, starter button 28 is not directly connected to manual reset thermostat 32. Upon closing lid 18, button extension 29 extends into starter button extension aperture 30 and only upon pressing while the lid is closed does the starter button extension 29 cooperate with actuator 31 of the thermostat 32. In order to prevent the leakage of moisture through the aperture 30, said aperture can be suitably covered with a flexible sheet such as a rubber sheet which would not hinder cooperation between the button extension and the actuator.

Although a manual reset thermostat is preferably employed, other positive temperature coefficient materials can be employed such as make or break thermostats.

An indicator element 34 in register with a clear lens 35 and lamp 36 disposed in lamp apperture 37 beneath the lens indicates whether the apparatus is in operation. Other indicator means may be suitably employed such as, for example, a temperature sensitive meter.

A thermostat 38 preferably an automatic thermostat maintains the indicator lamp 36 after the manual reset thermostat 32 deactivates heating element 33. After the disinfecting cycle has been completed and the apparatus has cooled to a suitable temperature, thermostat 38 automatically shuts off lamp 36 thereby indicating that the disinfecting cycle is complete and the contact lens carrying case containing the lenses can be removed.

In operation, a contact lens carrying case (not shown) typically containing a pair of hydrophilic contact lenses bathed in a saline solution is placed into the bottom portion heat member 16. By means of a male plug 41 the apparatus is connected to a line cord (not shown) and thence to a source of electricity. The cover 18 is closed thereby substantially completely enclosing the carrying case in a substantially heat tight compartment. The operator presses the starter button 28 which extends through the actuator aperture 30 thereby engaging the actuator 31 of the manual reset thermostat 32. The manual reset thermostat 32 actuates the heating element 33. The heating element 33 heats the heat member 16 until the heat member, which is preferably constructed of zinc, reaches a temperature of about +122° C. The manual reset thermostat 32 thereupon automatically and thermostatically deactivates the heating element 33. The interior of the carrying case is closely surrounded by the heating member and preferably the bottom and side walls of the carrying case are surrounded by the bottom portion heating member. The heat members transfer their absorbed heat to the carrying case thereby causing the temperature interior the carrying case to rise. The rate of heat transfer which, as explained hereinbefore, is such that the interior of the carrying case is maintained for a sufficient time and temperature so as to obtain a disinfecting cycle.

In order to indicate that apparatus 10 is in operation, indicator lamp 36 is automatically turned on upon activation of the heater element 33. When heat member 16 initially reaches a temperature of about +85° C, automatic thermostat 38 closes a switch so as to control the indicator lamp after the manual reset thermostat 32 deactivates the heating element. When the heating member 16 falls to a temperature of about +52° C, the indicator lamp 36 is automatically switched off by the thermostat 38 which opens thereby signaling that the lenses have been through a complete disinfecting cycle.

Accordingly, there is provided a process for disinfecting contact lenses by means of dry, hot air. The process comprises heating a contact lens carrying case, containing contact lenses bathed in a solution, by means of substantially dry, hot air i.e., air not heated by means of steam evolving from boiling water. The heat process is maintained at a temperature and for a period of time such that the contact lenses interior the case are subjected to a disinfecting cycle. Disinfecting cycle is understood to mean that period of time at the necessary temperatures required to destroy the pathogenic microorganisms on and about the contact lens.

Figure 5:
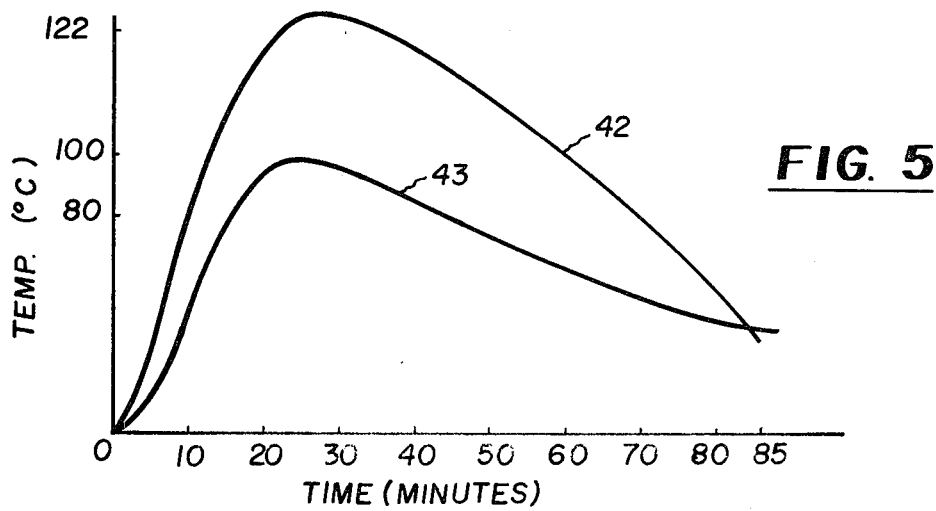
FIG. 5 is a temperature vs. time graph illustrating the temperature-time operation of the device of this invention.

FIG. 5 graphically illustrates the operation in accordance with the invention. Curve 42 represents the temperature-time curve of the heat member 16. Curve 43 represents the temperature-time curve interior the contact lens carrying case. At time zero both the interior of the carrying case and the heat member 16 are at about ambient temperature. The heat member 16 is selected from a material, preferably zinc, and constructed as to size, so as to reach the temperature of about +122° C in from about 5 to about 30 minutes and preferably about 15 minutes. As the temperature of the heat member 16 rises, it transfers its heat to the contact lens carrying case so that the interior of the carrying case typically reaches the temperature of about +80° C in about 15 minutes. Upon heat member 16 obtaining predetermined temperature of about +122° C, the heating element is deactivated. The heating member thereafter gives up its retained heat at a rate so as to maintain the interior of the carrying case at a temperature of between +80° C and about +100° C for at least a time required to disinfect the lenses. Typically the time required is about from 10 minutes and preferably to about 20 minutes. The temperature of the heat member and the carrying case thereafter slowly drops until the indicator light shows that the interior of the device has reached a temperature which permits comfortable handling. In order to insure that the heat member cannot be heated higher than the predetermined temperature thermal fuse 44 is employed.

We claim:

1. A hydrophilic contact lens disinfecting device for disinfecting contact lenses carried within a contact lens carrying case comprising in combination, means defining a housing having a base and a cover, said cover and said base being movable relative to each other, a well member received within said housing, said member adapted to receive a lens carrying case, said well member and said cover cooperating to define a compartment, means for heating said well member to a predetermined temperature, manual reset thermostat means for actuating said heating means and subsequently thermostatically deactivating said heating means upon said well member obtaining the predetermined temperature and substantially prior to the completion of a disinfecting cycle, said well member having a specific heat of from 0.09 to about 0.11 BTU/lb$_m$F° and a density of from about 445 to about 560 lb$_m$/ft.$^3$ whereby the heat transferred from the well to the contact lens carrying case received therein is sufficient to destroy pathogenic microorganisms contaminating a contact lens contained in the case.

2. The device of claim 1 wherein the well member is constructed of one of zinc, brass, copper, steel and grey iron.

3. A hydrophilic contact lens disinfecting device for disinfecting contact lenses carried within a contact lens carrying case comprising in combination, means defining a housing having a base and a cover, said cover and base being movable relative to each other, a heat storage-transfer block member received within said housing, said member adapted to receive a lens carrying case, said housing with said block member and said cover cooperating to define a compartment, means for heating said block member to a predetermined temperature which heat is transferred by said block member to the contact lens carrying case received therein to raise the interior temperature of the case to at least a disinfecting temperature, manual reset thermostat means for actuating said heating means and subsequently thermostatically deactivating said heating means upon the block member having obtained the predetermined temperature and substantially prior to the completion of a disinfecting cycle, said block member having a specific heat of from about 0.09 to about 0.11 BTU/lb$_m$F° and a density of from about 445 to about 560 lb$_m$/cu ft. whereby the heat absorbed by the member is transferred to the contact lens carrying case at a rate such that the disinfecting temperature is maintained interior the case for at least a disinfecting cycle.

4. The device of claim 3, wherein the predetermined temperature and the block member material is selected so as to maintain the disinfecting temperature interior the contact lens carrying case for at least ten minutes.

5. The device of claim 3, wherein the block member is recessed so as to substantially surround the bottom and side walls of a contact lens carrying case.

6. The device of claim 5 wherein the block member material is one of zinc, brass, steel, copper and grey iron.

7. The device of claim 6, wherein the block member material is zinc.

8. The device of claim 7, wherein the predetermined temperature is about +122° C.

9. A hydrophilic contact lens disinfecting device for disinfecting contact lenses carried within a contact lens carrying case comprising in combination, means defining a housing having a base and a cover, said cover and said base being movable relative to each other, a bottom portion heat storage-transfer block member received within said housing, said block member having a recess therein, said cover having molded on its underside and projecting downwardly therefrom a rim whereby when said cover is in closed position there is formed a substantially closed compartment adapted to contain a contact lens carrying case, means for heating said bottom portion block member to a predetermined temperature, which heat is transferred by said bottom portion block member to a contact lens carrying case received therein, manual reset thermostat activating said heating means and subsequently thermostatically deactivating said heating means upon the bottom block member obtaining the predetermined temperature and substantially prior to the completion of a disinfecting cycle, the bottom member material having a specific heat of from about 0.09 BTU/lb$_m$F° to about 0.11 BTU/lb$_m$F° and a density of from about 445 lb$_m$/cu ft. to about 560 lb$_m$/cu ft. whereby the heat absorbed by the bottom member is transferred to the carrying case at a rate such that the disinfecting temperature is maintained interior the contact lens carrying case for at least a disinfecting cycle.

10. The device of claim 9, further including indicator means for indicating the device is in an operating mode and deactivating means for the indicator.

11. The device of claim 10, wherein the indicator means is activated by means of the manually operable control means an upon deactivation of the heating means maintained by and deactivated by an automatic control means.

12. The device of claim 9, wherein the predetermined temperature and the block member material is selected so as to maintain an asepticizing temperature for at least ten minutes.

13. The device of claim 12, wherein the lower block member material is one of zinc, brass, steel, copper or grey iron.

14. The device of claim 12, wherein predetermined temperature is about +122° C.

* * * * *

UNITED STATES PATENT AND TRADEMARK OFFICE
CERTIFICATE OF CORRECTION

PATENT NO. : 4,044,226

DATED : August 23, 1977

INVENTOR(S) : John Kadlecik and Wayne R. Manning

It is certified that error appears in the above-identified patent and that said Letters Patent are hereby corrected as shown below:

Column 3, line 7, "560 $b_m/ft^3$" should be --560 $lb_m/ft^3$--

Column 4, line 15, "of" second occurrence should be --for--

Column 8, line 41, "an" should be --and--

Signed and Sealed this

Twenty-second Day of November 1977

[SEAL]

Attest:

RUTH C. MASON  
Attesting Officer

LUTRELLE F. PARKER  
Acting Commissioner of Patents and Trademarks